United States Patent
Li et al.

(10) Patent No.: US 10,577,621 B2
(45) Date of Patent: Mar. 3, 2020

(54) **TRANSIT PEPTIDE FROM *ARABIDOPSIS* CHLOROPLAST ATP SULFURYLASE 1 AND METHODS OF USE**

(71) Applicant: ACADEMIA SINICA, Taipei (TW)

(72) Inventors: Hsou-Min Li, Taipei (TW); Chiung-Chih Chu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/179,052

(22) Filed: Nov. 2, 2018

(65) Prior Publication Data

US 2019/0055573 A1    Feb. 21, 2019

Related U.S. Application Data

(62) Division of application No. 15/210,445, filed on Jul. 14, 2016, now Pat. No. 10,184,128.

(60) Provisional application No. 62/192,393, filed on Jul. 14, 2015.

(51) Int. Cl.
*C12N 15/82*    (2006.01)

(52) U.S. Cl.
CPC .............................. *C12N 15/8221* (2013.01)

(58) Field of Classification Search
None
See application file for complete search history.

(56) References Cited

PUBLICATIONS

Leustek et al. ATP sulfurylase 1, chloroplastic. (2014) UniProtKB/Swiss-Prot: Q9LIK9.1; pp. 1-4 (Year: 2014).*

* cited by examiner

*Primary Examiner* — Cathy Kingdon Worley
(74) *Attorney, Agent, or Firm* — WPAT, PC

(57) ABSTRACT

The present invention provides a recombinant DNA molecule encoding a fusion protein, comprising a first DNA sequence encoding a high-efficiency transit peptide operably linked to a second DNA sequence encoding a passenger protein, wherein the high-efficiency transit peptide is selected from the group consisting of transit peptides of the precursors of translocon at the inner envelope membrane of chloroplasts 40 kD (prTic40), chaperonin 10-2 (prCpn10-2), Fibrillin 1B (prFibrillin), ATP sulfurylase 1 (prAPS1), ATP sulfurylase 3 (prAPS3), 5'-adenylylsulfate reductase 3 (prAPR3), stromal ascorbate peroxidase (prsAPX), prTic40-E2A (a prTic40 variant), prCpn10-1-ΔC7C37S (a chaperonin 10-1 variant), a functional fragment of any of the transit peptides and an equivalent thereof. And the present invention also provides a method of high efficiency delivery of a protein into plastids using the high-efficiency transit peptides.

9 Claims, 5 Drawing Sheets

Specification includes a Sequence Listing.

SEQUENCE LISTING

```
<160> NUMBER OF SEQ ID NOS: 34

<210> SEQ ID NO 1
<211> LENGTH: 219
<212> TYPE: DNA
<213> ORGANISM: Pisum sativum

<400> SEQUENCE: 1
atggagaatc ttaacttagc ccttgtttct tccctaaac ccctgctttt aggacattcc      60
tcctcaaaaa acgttttctc aggaaggaag tctttcactt ttgggacgtt tcgcgtttct     120
gctaactctt catcctctca tgtcaccagg gctgcttcta aatctcacca aaatctaaaa     180
tctgtgcagg ggaaggtgaa tgcgcatgat tttgctagc                            219

<210> SEQ ID NO 2
<211> LENGTH: 129
<212> TYPE: DNA
<213> ORGANISM: Arabidopsis thaliana

<400> SEQUENCE: 2
atggcttcga gtttcattac agtacctaaa cccttcttgt ccttccccat caaaaccaat      60
gctcctactc tacctcagca gacccttctc ggaattcgaa gaaattcctt tagaattaac     120
gccgtttcc                                                             129

<210> SEQ ID NO 3
<211> LENGTH: 228
<212> TYPE: DNA
<213> ORGANISM: Arabidopsis thaliana

<400> SEQUENCE: 3
atggcgacgg tacaattgtc cacccaattt agctgccaaa ccagagtttc aatctcaccg      60
aactctaaat ctatctccaa gcctccgttt ctggtaccgg tgacctcaat tattcaccgc     120
ccgatgatct ccaccggagg aatcgctgtt tccccccgta gagttttcaa agtccgagcc     180
acagatacgg gagagatagg atcagctcta ttggcggcgg aggaagca                  228

<210> SEQ ID NO 4
<211> LENGTH: 222
<212> TYPE: DNA
<213> ORGANISM: Arabidopsis thaliana

<400> SEQUENCE: 4
atggcttcaa tggctgccgt cttaagcaaa actccattcc tctctcaacc actaaccaaa      60
tcatctccaa actccgatct ccccttcgcc gcggtttcct tcccttccaa atccctacgc     120
```

```
cgccgcgtag gatcaatccg agccggatta atcgctcccg acggtggtaa gcttgtagag    180
ctcatcgtgg aagagccaaa gcggcgagag aagaaacacg ag                      222
```

<210> SEQ ID NO 5
<211> LENGTH: 222
<212> TYPE: DNA
<213> ORGANISM: Arabidopsis thaliana

<400> SEQUENCE: 5

```
atggcttcca tgtccaccgt cttccccaaa ccaacctctt tcatctctca acctctaaca    60
aaatctcaca aatccgattc cgtaaccaca tccatttcat tcccttcgaa ttcgaaaact   120
cgtagcttaa gaaccatctc tgtacgagct ggcttaatcg agccagatgg tgggaaactt   180
gtggatcttg ttgtaccgga accgagacgg cgagagaaga aa                      222
```

<210> SEQ ID NO 6
<211> LENGTH: 249
<212> TYPE: DNA
<213> ORGANISM: Arabidopsis thaliana

<400> SEQUENCE: 6

```
atggcactag caatcaacgt ttcttcatct tcttcttctg cgatctcaag ctctagcttc    60
ccttcttcag atctcaaagt aacaaaaatc ggatcattga ggttattgaa tcgtaccaat   120
gtctctgcgg cttctctgag tttgtccggg aagagatcct ccgtgaaagc tcttaatgtg   180
caatcaatta caaaggaatc cattgttgct tctgaggtta cagagaagct agatgtggtg   240
gaagttgaa                                                           249
```

<210> SEQ ID NO 7
<211> LENGTH: 150
<212> TYPE: DNA
<213> ORGANISM: Arabidopsis thaliana

<400> SEQUENCE: 7

```
atggcagagc gtgtgtctct cacactcaac ggaaccctcc tttctcctcc tcccacaaca    60
acaacaacaa caatgtcttc ttctctccga tctaccaccg ccgcttctct tctcctccgc   120
tcctcctcct cctcctccag atccactctc                                    150
```

<210> SEQ ID NO 8
<211> LENGTH: 219
<212> TYPE: DNA
<213> ORGANISM: Arabidopsis thaliana

<400> SEQUENCE: 8

```
atggcgaatc ttaacttagc ccttgtttct tcccctaaac ccctgctttt aggacattcc    60
tcctcaaaaa acgttttctc aggaaggaag tctttcactt tgggacgtt tcgcgttttct   120 gctaactctt catcctctca tgtcaccagg gctgcttcta atctcaccca aaatctaaaa   180
tctgtgcagg ggaaggtgaa tgcgcatgat tttgctagc                          219
```

<210> SEQ ID NO 9
<211> LENGTH: 129
<212> TYPE: DNA
<213> ORGANISM: Arabidopsis thaliana

```
<400> SEQUENCE: 9
atggcttcca ctttcgtctc tctaccaaat cctttctttg cttttccggt caaagcaact    60
actccttcga cggctaacca tacgcttctc ggaagtcgaa gaggttccct tagaatcaaa   120
gcgatttcc                                                           129

<210> SEQ ID NO 10
<211> LENGTH: 73
<212> TYPE: PRT
<213> ORGANISM: Pisum sativum

<400> SEQUENCE: 10

Met Glu Asn Leu Asn Leu Ala Leu Val Ser Ser Pro Lys Pro Leu Leu
1               5                   10                  15

Leu Gly His Ser Ser Lys Asn Val Phe Ser Gly Arg Lys Ser Phe
            20                  25                  30

Thr Phe Gly Thr Phe Arg Val Ser Ala Asn Ser Ser Ser His Val
        35                  40                  45

Thr Arg Ala Ala Ser Lys Ser His Gln Asn Leu Lys Ser Val Gln Gly
    50                  55                  60

Lys Val Asn Ala His Asp Phe Ala Ser
65                  70

<210> SEQ ID NO 11
<211> LENGTH: 43
<212> TYPE: PRT
<213> ORGANISM: Arabidopsis thaliana

<400> SEQUENCE: 11

Met Ala Ser Ser Phe Ile Thr Val Pro Lys Pro Phe Leu Ser Phe Pro
1               5                   10                  15

Ile Lys Thr Asn Ala Pro Thr Leu Pro Gln Gln Thr Leu Leu Gly Ile
            20                  25                  30

Arg Arg Asn Ser Phe Arg Ile Asn Ala Val Ser
        35                  40

<210> SEQ ID NO 12
<211> LENGTH: 76
<212> TYPE: PRT
<213> ORGANISM: Arabidopsis thaliana

<400> SEQUENCE: 12

Met Ala Thr Val Gln Leu Ser Thr Gln Phe Ser Cys Gln Thr Arg Val
1               5                   10                  15

Ser Ile Ser Pro Asn Ser Lys Ser Ile Ser Lys Pro Pro Phe Leu Val
            20                  25                  30

Pro Val Thr Ser Ile Ile His Arg Pro Met Ile Ser Thr Gly Gly Ile
        35                  40                  45

Ala Val Ser Pro Arg Arg Val Phe Lys Val Arg Ala Thr Asp Thr Gly
    50                  55                  60

Glu Ile Gly Ser Ala Leu Leu Ala Ala Glu Glu Ala
65                  70                  75

<210> SEQ ID NO 13
<211> LENGTH: 74
<212> TYPE: PRT
<213> ORGANISM: Arabidopsis thaliana
```

```
<400> SEQUENCE: 13

Met Ala Ser Met Ala Ala Val Leu Ser Lys Thr Pro Phe Leu Ser Gln
1               5                   10                  15

Pro Leu Thr Lys Ser Ser Pro Asn Ser Asp Leu Pro Phe Ala Ala Val
            20                  25                  30

Ser Phe Pro Ser Lys Ser Leu Arg Arg Val Gly Ser Ile Arg Ala
        35                  40                  45

Gly Leu Ile Ala Pro Asp Gly Gly Lys Leu Val Glu Leu Ile Val Glu
    50                  55                  60

Glu Pro Lys Arg Arg Glu Lys Lys His Glu
65                  70

<210> SEQ ID NO 14
<211> LENGTH: 74
<212> TYPE: PRT
<213> ORGANISM: Arabidopsis thaliana

<400> SEQUENCE: 14

Met Ala Ser Met Ser Thr Val Phe Pro Lys Pro Thr Ser Phe Ile Ser
1               5                   10                  15

Gln Pro Leu Thr Lys Ser His Lys Ser Asp Ser Val Thr Thr Ser Ile
            20                  25                  30

Ser Phe Pro Ser Asn Ser Lys Thr Arg Ser Leu Arg Thr Ile Ser Val
        35                  40                  45

Arg Ala Gly Leu Ile Glu Pro Asp Gly Gly Lys Leu Val Asp Leu Val
    50                  55                  60

Val Pro Glu Pro Arg Arg Arg Glu Lys Lys
65                  70

<210> SEQ ID NO 15
<211> LENGTH: 83
<212> TYPE: PRT
<213> ORGANISM: Arabidopsis thaliana

<400> SEQUENCE: 15

Met Ala Leu Ala Ile Asn Val Ser Ser Ser Ser Ser Ala Ile Ser
1               5                   10                  15

Ser Ser Ser Phe Pro Ser Ser Asp Leu Lys Val Thr Lys Ile Gly Ser
            20                  25                  30

Leu Arg Leu Leu Asn Arg Thr Asn Val Ser Ala Ala Ser Leu Ser Leu
        35                  40                  45

Ser Gly Lys Arg Ser Ser Val Lys Ala Leu Asn Val Gln Ser Ile Thr
    50                  55                  60

Lys Glu Ser Ile Val Ala Ser Glu Val Thr Glu Lys Leu Asp Val Val
65                  70                  75                  80

Glu Val Glu

<210> SEQ ID NO 16
<211> LENGTH: 50
<212> TYPE: PRT
<213> ORGANISM: Arabidopsis thaliana

<400> SEQUENCE: 16

Met Ala Glu Arg Val Ser Leu Thr Leu Asn Gly Thr Leu Leu Ser Pro
1               5                   10                  15

Pro Pro Thr Thr Thr Thr Thr Met Ser Ser Ser Leu Arg Ser Thr
            20                  25                  30
```

```
Thr Ala Ala Ser Leu Leu Leu Arg Ser Ser Ser Ser Ser Arg Ser
         35                  40                  45

Thr Leu
 50
```

<210> SEQ ID NO 17
<211> LENGTH: 73
<212> TYPE: PRT
<213> ORGANISM: Arabidopsis thaliana

<400> SEQUENCE: 17

```
Met Ala Asn Leu Asn Leu Ala Leu Val Ser Ser Pro Lys Pro Leu Leu
 1               5                  10                  15

Leu Gly His Ser Ser Lys Asn Val Phe Ser Gly Arg Lys Ser Phe
             20                  25                  30

Thr Phe Gly Thr Phe Arg Val Ser Ala Asn Ser Ser Ser His Val
         35                  40                  45

Thr Arg Ala Ala Ser Lys Ser His Gln Asn Leu Lys Ser Val Gln Gly
     50                  55                  60

Lys Val Asn Ala His Asp Phe Ala Ser
65                  70
```

<210> SEQ ID NO 18
<211> LENGTH: 43
<212> TYPE: PRT
<213> ORGANISM: Arabidopsis thaliana

<400> SEQUENCE: 18

```
Met Ala Ser Thr Phe Val Ser Leu Pro Asn Pro Phe Phe Ala Phe Pro
 1               5                  10                  15

Val Lys Ala Thr Thr Pro Ser Thr Ala Asn His Thr Leu Leu Gly Ser
             20                  25                  30

Arg Arg Gly Ser Leu Arg Ile Lys Ala Ile Ser
         35                  40
```

<210> SEQ ID NO 19
<211> LENGTH: 174
<212> TYPE: DNA
<213> ORGANISM: Arabidopsis thaliana

<400> SEQUENCE: 19

```
atggcttcct caatgatctc ctccccagct gttaccaccg tcaaccgtgc cggtgccggc      60
atggttgctc cattcaccgg cctcaaatcc atggctggct cccccacgag gaagaccaac     120
aatgacatta cctccattgc tagcaacggt ggaagagtac aatgcatgca ggtg           174
```

<210> SEQ ID NO 20
<211> LENGTH: 58
<212> TYPE: PRT
<213> ORGANISM: Arabidopsis thaliana

<400> SEQUENCE: 20

```
Met Ala Ser Ser Met Ile Ser Ser Pro Ala Val Thr Thr Val Asn Arg
 1               5                  10                  15

Ala Gly Ala Gly Met Val Ala Pro Phe Thr Gly Leu Lys Ser Met Ala
             20                  25                  30

Gly Phe Pro Thr Arg Lys Thr Asn Asn Asp Ile Thr Ser Ile Ala Ser
         35                  40                  45

Asn Gly Gly Arg Val Gln Cys Met Gln Val
     50                  55
```

```
<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgaagcttat ggcgacggta caattgtc                                            28

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgctgcagtc aaggattcaa gagagg                                              26

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cactcgagat ggcttccatg tccaccgtct tcc                                      33

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagtcgactt aaaccggaat cttttccgga agtt                                     34

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agctcgagat ggcagagcgt gtgtctc                                             27

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgtcgactt agataacgat accctccg                                            28
```

```
<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctcttgaat cctatgatgt gactgcaggt cg                                    32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgacctgcag tcacatcata ggattcaaga ga                                    32

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgataagctt gatatggcga atcttaactt agccc                                 35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggctaagtt aagattcgcc atatcaagct tatcg                                 35

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcttccactt tcgtctctct accaaatcct                                       30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggatttggt agagagacga aagtggaagc                                       30
```

```
<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cggaagtcga agaggttccc ttagaatcaa agcga                              35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcgctttgat tctaagggaa cctcttcgac ttccg                              35
```

TRANSIT PEPTIDE FROM *ARABIDOPSIS* CHLOROPLAST ATP SULFURYLASE 1 AND METHODS OF USE

CROSS-REFERENCES TO RELATED APPLICATIONS

This application is a Divisional of co-pending U.S. application Ser. No. 15/210,445, filed on Jul. 14, 2016, which claims the priority benefit of Provisional Application No. 62/192,393, filed on 14 Jul. 2015; the entire contents of all of the above-identified applications are incorporated herewith by reference.

SEQUENCE LISTING

The instant application contains a Sequence Listing which has been submitted electronically in ASCII format and is hereby incorporated by reference in its entirety.

BACKGROUND OF THE INVENTION

1. Field of the Invention

The present invention relates to plant biotechnology. More particularly, the present invention relates a method for high efficiency protein delivery into plastids, in particular, leucoplasts.

2. The Prior Arts

Plastids are essential organelles in plants responsible for functions ranging from photosynthesis, biosynthesis of all fatty acids, starch, carotenoids, and most amino acids, to assimilation of nitrogen and sulfur. Plastids differentiate into different functional types in different tissues, for example chloroplasts in green tissues for photosynthesis, chromoplasts in petals and fruits for carotenoid pigments accumulation, and leucoplasts in non-green tissues for synthesis and storage of nutrients, including starch, proteins and oils. To perform these specific functions, different types of plastids require, and therefore import, different proteins.

Although plastids have their own genome, most plastid proteins are encoded by the nuclear genome, synthesized in the cytosol as a larger precursor with an N-terminal extension called the transit peptide. Transit peptides are necessary and sufficient for targeting passenger proteins into plastids, i.e., a transit peptide can be taken from the original precursor and fused to a passenger protein and results in delivery of the passenger protein into plastids. Transit peptides that can deliver passenger proteins into chloroplasts with high efficiency, for example the transit peptide of RuBP carboxylase small subunit precursor (prRBCS), have been identified and used to deliver passenger proteins into plastids.

Most grain- and root-type food crops, for example rice, corn and cassava, use leucoplasts to synthesize and store the starch that is used to feed the majority of the world population. However, despite the economic importance of leucoplasts, almost all of our knowledge about plastid protein import is derived from studies with chloroplasts and little is known about how proteins are imported into leucoplasts. Unfortunately, leucoplasts clearly have a different substrate preference, and transit peptides like that of prRBCS import proteins poorly into leucoplasts. For example, it has been shown that the transit peptide of prRBCS could not direct the import of the passenger protein green fluorescent protein (GFP) into leucoplasts in endosperms of transgenic wheat (Primavesi et al., 2008). Using leucoplasts isolated from castor seeds and chloroplasts isolated from pea, it has been shown that prRBCS imported much better into chloroplasts than into leucoplasts (Wan et al., 1996). Using leucoplasts and chloroplasts isolated from pea roots and leaves, respectively, it has been shown that prRBCS could not be imported into leucoplasts at all (Yan et al., 2006). Nonetheless, in these studies, no proper quantitative comparisons were performed so the import efficiency of transit peptides could not be compared directly among one another. Therefore the exact import efficiency of prRBCS transit peptide into leucoplasts is not known and no transit peptides with high leucoplast import efficiency have been discovered.

The transit peptide for prRBCS is the most widely used transit peptide for delivering engineered proteins into plastids in biotechnology applications. Examples include the famous Golden Rice, Roundup Ready® corn and Dicamba resistant soybean. As discussed above, many reports have suggested that this transit peptide deliver proteins poorly into leucoplasts and therefore is not the best transit peptide for applications that need to express proteins in leucoplasts. However, no report has performed quantitative comparisons between transit peptides. If quantitative comparison can be performed and transit peptides with higher leucoplast import efficiency than prRBCS transit peptide can be identified, these new transit peptides would be valuable tools for delivering engineered proteins into leucoplasts.

SUMMARY OF THE INVENTION

The present invention relates to a recombinant DNA molecule encoding a fusion protein comprising a first DNA sequence encoding a high-efficiency transit peptide operably linked to a second DNA sequence encoding a passenger protein, a DNA construct comprising said recombinant DNA molecule operably linked to a promoter, a plant material comprising said DNA construct or said recombinant DNA molecule, and a method for high efficiency protein delivery into plastids, in particular, leucoplasts, using said recombinant DNA molecule or said construct.

Leucoplasts are plastids essential for the synthesis and storage of starch, lipids and proteins. Most grain and root-type crops use leucoplasts to synthesize and store nutrients. Modifications of the biosynthesis processes within leucoplasts to better suit human needs will require high efficiency delivery of engineered proteins into leucoplasts. Many reports have shown that proteins that could import efficiently into chloroplasts import poorly into leucoplasts because the two plastids have different protein preference. However, most plastid-targeting transit peptides currently available are derived from precursor proteins with high chloroplast import efficiency. No transit peptide with high leucoplast import efficiency is available. To identify transit peptides with high leucoplast import efficiency, the present invention first optimized the in vitro leucoplast import system to allow fast, quantitative and accurate comparisons of import efficiencies of a large number of plastid precursor proteins. Using this leucoplast import system, the present invention identified a group of nine precursor proteins that have very high import efficiency into leucoplasts and chloroplasts. These precursors imported into chloroplasts equally well or better than prRBCS, but imported into leucoplasts two to eight times better than prRBCS, whose transit peptide is currently the most widely used transit peptide for directing engineered proteins into all plastids, including leucoplasts.

An objective of the present invention is to provide a recombinant DNA molecule encoding a fusion protein, wherein said recombinant DNA molecule comprising a first DNA sequence encoding a high-efficiency transit peptide operably linked to a second DNA sequence encoding a passenger protein, wherein the high-efficiency transit peptide is selected from the group consisting of the transit peptides of the precursors of translocon at the inner envelope membrane of chloroplasts 40 kD (prTic40), chaperonin 10-2 (prCpn10-2), Fibrillin 1B (prFibrillin), ATP sulfurylase 1 (prAPS1), ATP sulfurylase 3 (prAPS3), 5'-adenylylsulfate reductase 3 (prAPR3), stromal ascorbate peroxidase (prsAPX), prTic40-E2A (a prTic40 variant), prCpn10-1-ΔC7C37S (a chaperonin 10-1 variant), a functional fragment of any of said transit peptides and an equivalent thereof.

Another objective of the present invention is to provide a DNA construct comprising the recombinant DNA molecule encoding a fusion protein as described herein, operably linked to a promoter.

Another objective of the present invention is to provide a plant material transformed with, and comprising the DNA construct.

Another objective of the present invention is to provide a method of high efficiency delivery of a passenger protein into plastids of the transformed plant material, comprising: providing a recombinant DNA molecule encoding a fusion protein; linking the recombinant DNA molecule operably with a promoter to form a DNA construct; and transforming the DNA construct into a plant material to express the fusion protein, wherein the recombinant DNA molecule comprises a first DNA sequence encoding a high-efficiency transit peptide operably linked to a second DNA sequence encoding the passenger protein, wherein the high-efficiency transit peptide is selected from the group consisting of the transit peptides of the precursors of translocon at the inner envelope membrane of chloroplasts 40 kD (prTic40), chaperonin 10-2 (prCpn10-2), Fibrillin 1B (prFibrillin), ATP sulfurylase 1 (prAPS1), ATP sulfurylase 3 (prAPS3), 5'-adenylylsulfate reductase 3 (prAPR3), stromal ascorbate peroxidase (prsAPX), prTic40-E2A (a prTic40 variant), prCpn10-1-ΔC7C37S (a chaperonin 10-1 variant), a functional fragment of any of said transit peptides and an equivalent thereof.

In one embodiment of the present invention, the first DNA sequence encoding a high-efficiency transit peptide is selected from the group consisting of SEQ ID NO:10 to SEQ ID NO:18, a functional fragment of any of said SEQ ID NOs and an equivalent thereof.

In one embodiment of the present invention, the high-efficiency transit peptides as described herein are capable of delivering an amount of passenger proteins that is equal or higher than the amount of passenger proteins a prRBCS transit peptide is capable of delivering into chloroplasts, and are capable of delivering an amount of passenger proteins that is higher than the amount of passenger proteins a prRBCS transit peptide is capable of delivering into leucoplasts.

In one embodiment of the present invention, the passenger protein is a biologically-active protein. In another embodiment, the passenger protein is a protein to be delivered to plastids.

In one embodiment of the present invention, the promoter is functional in a plant cell.

In one embodiment of the present invention, the plant material is selected from the group consisting of a plant cell, a plant tissue, a plant tissue culture, a callus culture and a transgenic plant.

In one embodiment of the present invention, the plant material is obtained from a monocotyledon or a dicotyledon plant.

Accordingly, the nine transit peptides of the present invention, including transit peptides of the precursors of the translocon at the inner envelope membrane of chloroplasts 40 kD (prTic40) (SEQ ID NO:10), chaperonin 10-2 (prCpn10-2) (SEQ ID NO:11), Fibrillin 1B (prFibrillin) (SEQ ID NO:12), ATP sulfurylase 1 (prAPS1) (SEQ ID NO:13), ATP sulfurylase 3 (prAPS3) (SEQ ID NO:14), 5'-adenylylsulfate reductase 3 (prAPR3) (SEQ ID NO:15), stromal ascorbate peroxidase (prsAPX) (SEQ ID NO:16), prTic40-E2A (a prTic40 variant) (SEQ ID NO:17) and prCpn10-1-ΔC7C37S (a chaperonin 10-1 variant) (SEQ ID NO:18), provide a valuable tool to enable high efficiency delivery of engineered proteins into plastids for all kinds of plants.

BRIEF DESCRIPTION OF THE DRAWINGS

In FIG. 1A, leucoplasts and chloroplasts were isolated from roots of 4-day-old pea seedlings grown in the dark and leaves of 7-day-old pea seedlings grown under 12-h photoperiod, respectively. The isolated leucoplasts (500 or 113.67 μg protein) and chloroplasts (500 μg protein) were incubated under import conditions with 18 μL in vitro-translated [$^{35}$S]Met-prTic40 or [$^{35}$S]Met-prRBCS and 3 mM ATP in import buffer in a final volume of 200 μL for 25 min. The two different concentrations of leucoplasts, 500 and 113.67 μg of protein, are for comparing with chloroplasts based on equal amounts of proteins and equal numbers of plastids, respectively. 500 μg of leucoplasts have the same amount of proteins as 500 μg of chloroplasts, while 113.67 μg of leucoplasts have the same number of plastids as 500 μg of chloroplasts. After import, intact leucoplasts and chloroplasts were re-isolated through a 10% and 40% Percoll cushion, respectively. The import samples were analyzed by SDS-PAGE, stained with Coomassie blue, and dried for fluorography. 4% of the plastids in each import reaction (20 μg or 4.55 μg of proteins) were loaded. Tr, 1% of the in vitro-translated precursor proteins used in each import reaction. In FIG. 1B, the imported mature proteins in experiments as those shown in FIG. 1A were quantified and the import efficiencies were calculated. Data shown are mean±SD of three independent experiments. Cpt, chloroplasts; Leu, leucoplasts. pr, precursor protein; m, mature protein derived after import.

In FIG. 2A, isolated leucoplasts (113.67 μg protein) and chloroplasts (500 μg protein) were incubated with in vitro-translated prFd-protein A, prPDH E1α, or prCpn10-2 under import conditions for 25 min. After import, intact leucoplasts and chloroplasts were re-isolated through a 10% and 40% Percoll cushion, respectively. The import samples were analyzed by SDS-PAGE, stained with Coomassie blue, and dried for fluorography. 4% of the plastids in each import reaction were loaded. Tr, 1% (for prFd-protein A and prPDH E1α) or 1.2% (for prCpn10-2) of the in vitro-translated precursor proteins used in the import reactions. In FIG. 2B, imported mature proteins in experiments as those shown in FIG. 2A were quantified and the import efficiencies were calculated. Data shown are mean±SD of three independent experiments. Cpt, chloroplasts; Leu, leucoplasts. pr, precursor protein; m, mature protein derived after import.

In FIG. 3A, isolated leucoplasts (113.67 µg proteins) and chloroplasts (500 µg proteins) were incubated with in vitro-translated [$^{35}$S]Met-precursor proteins under import conditions for 25 min. After import, intact leucoplasts and chloroplasts were re-isolated through a 10% and 40% Percoll cushion, respectively. The samples were analyzed by SDS-PAGE, stained with Coomassie blue, and dried for fluorography. 4% of the plastids in each import reaction were loaded. Tr, 1.2% of the in vitro-translated precursor proteins used in each import reaction. pr, precursor protein; m, mature protein derived after import. In FIGS. 3B and 3C, imported mature proteins in chloroplasts (3B) and leucoplasts (3C) in experiments as those shown in FIG. 3A were quantified and the import efficiency of each precursor was calculated. The import efficiency of prRBCS was set as 1. Data shown are mean±SD of at least three independent experiments. Cpt, chloroplasts; Leu, leucoplasts.

In FIG. 4A, protoplasts isolated from tobacco BY2 cells were co-transformed with GFP or transit-peptide-GFP fusion plasmids and the plasmid pBI221, which directed the expression of β-glucuronidase (GUS) in the cytosol and served as an internal control for transformation and protein expression efficiency. After transformation, the protoplasts were incubated in the dark at 25° C. for 16 h, analyzed by SDS-PAGE and immunodetected with antibodies indicated on the left. Thirty micrograms of proteins were loaded in each lane. Plasmid DNA used for each lane is labeled at the top. Lane 1, control protoplasts with no plasmid DNA added during the transformation. Lane 2, protoplasts transformed with pBI221 and the GFP vector without fusing to any transit peptide. Lanes 3 to 12, protoplasts transformed with pBI221 and a plasmid encoding GFP fused to prRBCS transit peptide (lane 3), or GFP fused to one of the nine transit peptides of the present invention (lanes 4 to 12). The transit peptide part is indicated with subscript "tp". Filled circles mark the precursor form of each fusion protein and brackets mark GFP imported into BY2 cell leucoplasts. In FIG. 4B, the amount of GUS and imported GFP in experiments as those shown in FIG. 4A were quantified. The efficiency of each transit peptide was calculated by the amount of GFP normalized to the amount of GUS in the same sample. The GFP/GUS ratio of RBCS$_{tp}$-GFP was set as 1. Data shown are mean±SD of two independent experiments.

DETAILED DESCRIPTION OF THE PREFERRED EMBODIMENT

Figure 1A:
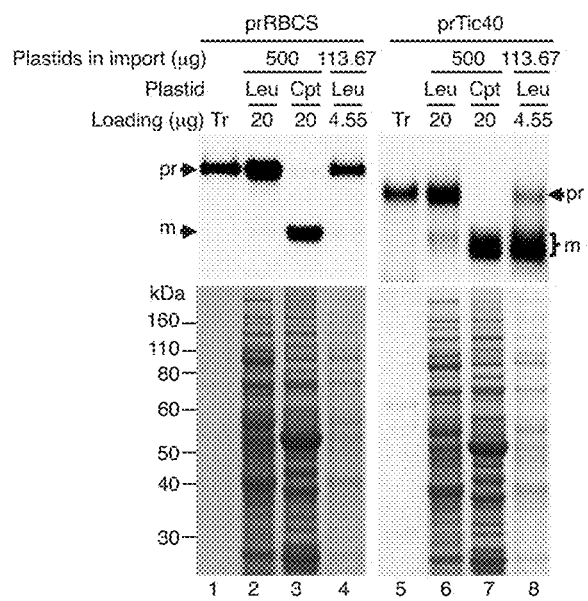
FIGS. 1A and 1B show that prRBCS imported much less efficiently into leucoplasts than into chloroplasts no matter whether the comparison was done based on equal proteins or on equal plastids, and prTic40 had much higher leucoplast import efficiencies than prRBCS.

The accompanying drawings are included to provide a further understanding of the invention, and are incorporated in and constitute a part of this specification. The drawings illustrate embodiments of the invention and, together with the description, serve to explain the principles of the invention.

As a first step in identifying precursors with high leucoplast import efficiency, the present invention optimized the in vitro leucoplast protein import system for higher efficiency import and fast, accurate and quantitative comparisons, between leucoplasts and chloroplasts, and among transit peptides. A group of nine precursors that imported into chloroplasts equally well as prRBCS, but imported into leucoplasts much more efficiently than prRBCS, were identified. The present invention further showed that a higher amount of passenger proteins were imported into leucoplasts in vivo when the passenger protein was fused to these high efficiency transit peptides of the present invention, than when fused to the prRBCS transit peptide.

Definition

Unless otherwise defined, all technical and scientific terms used herein have the same meaning as commonly understood by one of ordinary skill in the art to which this invention pertains. In the case of conflict, the present document, including definitions will control.

As used herein, promoters suitable for the practice of this invention include all promoters that have been shown to drive RNA expression in plants, including those that are constitutive, inducible or tissue-specific. Examples include, but are not limited to, maize RS81 promoter, rice ubiquitin promoters, rice glutelin (Gt1) promoter, maize RS324 promoter, maize PR-1 promoter, maize A3 promoter, maize L3 oleosin promoter, rice actin promoters, prRBCS promoter, phytoene desaturase promoter, sporamin promoter, gamma-coixin promoter, maize chloroplast aldolase promoter, nopaline synthase (NOS) promoter, octopine synthase (OCS) promoter, cauliflower mosaic virus (CaMV) 19S and 35S promoters, figwort mosaic virus 35S promoter, *Arabidopsis* sucrose synthase promoter, R gene complex promoter, chlorophyll a/b binding protein gene promoter, CaMV35S promoter with enhancer sequences e35S, FMV35S promoter, FLt36 promoter of peanut chlorotic streak virus, At.Act 7 promoter, At.ANT1 promoter, FMV.35S-EF1a promoter, eIF4A10 promoter, AGRtu.nos promoter, and rice cytosolic triose phosphate isomerase promoter.

As used herein, passenger proteins suitable for the practice of this invention are any protein the one of ordinary skill in the art wishes to express in plastids. Examples include, but are not limited to, GFP, β-glucuronidase (GUS), dicamba monooxygenase (DMO), enolpyruvyl shikimate-3-phosphate (EPSP) synthase, glyphosate oxidase (GOX), phytoene synthase (psy), AtOR (R90H) (the R90H mutant of *Arabidopsis* ORANGE protein), β-carotene ketolase and phytoene desaturase.

As used herein, "monocotyledon plant" refers to any of a class of angiosperm plants having a single cotyledon in the seed, and includes (but is not limited to) rice, rye, wheat, barley, sorghum, maize, oat, orchids, lily, banana, taro and sugar cane.

As used herein, "dicotyledon plant" refers to an angiosperm that is not a monocotyledon, having two cotyledons in the seed, and includes (but is not limited to) *Arabidopsis*, tobacco, potato, sweet potato, canola, soybean, bean, cotton, sunflower, white cauliflower, *chrysanthemum*, cassava and roses.

As used herein, a "high-efficiency" transit peptide refers to a transit peptide which is capable of delivering an amount of passenger proteins that is equal or higher than the amount of passenger proteins a prRBCS transit peptide is capable of delivering into chloroplasts, and is capable of delivering an amount of passenger proteins that is higher than the amount of passenger proteins a prRBCS transit peptide is capable of delivering into leucoplasts. The method used for comparing the amounts of passenger proteins being delivered into different groups of chloroplasts and leucoplasts can be the optimized method as described herein, or any such method that is capable of differentiating between a higher and a lower amount of a particular protein that has accumulated in chloroplasts and leucoplasts of at least two experimental groups of cells.

As used herein, the terms "construct" and "vector" are used interchangeably.

Transit peptides are known to function across species. For example, the prRBCS transit peptide from pea was used in the Golden rice creation. The pea prRBCS transit peptide is also used in creating the Dicamba resistant soybean and the initial studies for the creation were performed in *Arabidopsis* and tobacco. The prRBCS transit peptide from *Arabidopsis* was used in the Roundup Ready® corn (USDA, 1996). A transit peptide from the waxy protein of corn was shown to function well in potato. For the current invention, the high-efficiency transit peptides were identified from pea and *Arabidopsis* and the initial tests were performed in pea, tobacco and rice and will also be tested in *Arabidopsis*. It is expected that these nine transit peptides of the present invention will provide high efficiency delivery of proteins into leucoplasts of all monocotyledon and dicotyledon plants, for example leucoplasts in the tubers, endosperms and roots of rice, barley, wheat, corn, cassava, potato and soybean and into leucoplasts of white colored petals of all flowers. Furthermore, because precursors containing these transit peptides also import very efficiently into chloroplasts, these transit peptides will also be expected to deliver proteins into chloroplasts with high efficiency.

EXAMPLE 1

Plastid Isolation, Protein Concentration Assays, and Plastid Number Counting

Pea seedlings (*Pisum sativum* cv. Green Arrow) were grown at 20° C. on vermiculite. Leucoplasts were prepared from roots of 4- to 5-day-old dark grown seedlings as described (Chu and Li, 2015). Chloroplasts were isolated from leaves of 7-day-old seedlings grown under a 12-h photoperiod with a light intensity of approximately 150 µmol m$^{-2}$ s$^{-1}$ as described (Perry et al., 1991), except 2 mM ascorbic acid, 0.1 mM dithiothreitol, and 1.2 mM glutathione were added in the grinding buffer used for homogenization. Isolated chloroplasts were adjusted to 1 mg chlorophyll mL$^{-1}$ in import buffer.

EXAMPLE 2

Optimization of the Protocol for Isolation of Import-competent Leucoplasts

To set up a quantitative leucoplast import system, the present invention first optimized the conditions for leucoplast isolation. The present invention increased the concentration of EDTA and BSA in the homogenization buffer and also added reducing agents into the buffer. After these modifications, the import efficiencies of precursor proteins into isolated leucoplasts were increased (Chu and Li, 2015).

EXAMPLE 3

Plasmid Construction and in Vitro Translation of Precursors for in Vitro Import into Isolated Plastids Plasmids encoding prRBCS, prTic40, prFd-protein A, prPDH E1α, and prCpn10-2 have been described (Teng et al., 2012). The cDNA clones of pda02149 for precursor of ATP sulfurylase 1 (prAPS1, AT3G22890) and pda04912 for precursor of 5'-adenylylsulfate reductase 3 (APR3, AT4G21990) were obtained from RIKEN BioResource Center. The leaf cDNA pools of *Arabidopsis thaliana* (Columbia ecotype) were used as templates to amplify the coding regions of Fibrillin 1B precursor (prFibrillin, AT4G22240), ATP sulfurylase 3 precursor (prAPS3, AT4G14680), and stromal ascorbate peroxidase precursor (prsAPX, AT4G08390) with specific forward and reverse primer pairs as described in Table 1. The PCR products of prFibrillin were digested with HindIII and PstI and cloned into the HindIII/PstI of pSP72. The PCR products of prAPS3 and prsAPX were digested with XhoI and SalI and cloned into the XhoI/SalI site of pSP72, respectively. The sequences of prFibrillin, prAPS3, and prsAPX were confirmed by sequencing and the plasmid was named pSP72-Fibrillin, pSP72-APS3, and pSP72-sAPX, respectively. Since the prFibrillin has only two Met in the transit peptide region, the sequence encoding 2 extra Met were inserted into the 3'end of cDNA before the stop codon using the QuikChange II Site-Directed Mutagenesis Kit (AGILENT TECHNOLOGIES) with primers fibrillin-2M-F and fibrillin-2M-R (Table 1). The sequence was confirmed by sequencing and the plasmid was named pSP72-Fibrillin-2M and this plasmid was used in the subsequent analyses. The prTic40 cording region in the pBS plasmid was digested with XhoI and PstI and cloned into the XhoI/PstI site of pSP72 to generate the pSP72-Tic40 plasmid. This pSP72-Tic40 construct was used to generate the prTic40 variant using the QuikChange II Site-Directed Mutagenesis Kit (AGILENT TECHNOLOGIES) with primers pSP72-Tic40-E2A-F and pSP72-Tic40-E2A-R (Table 1). The sequence was confirmed by sequencing and the plasmid was named pSP72-Tic40-E2A. For the prCpn10-1 variant, prCpn10-1-ΔC7C37S, the prCpn10-1 plasmid (Teng et al., 2012) was used for site-directed mutagenesis via the QuikChange II Site-Directed Mutagenesis Kit (AGILENT TECHNOLOGIES) with primers Cpn10-1-ΔC7-F and Cpn10-1-ΔC7-R to generate the plasmid pSP72-Cpn10-1-ΔC7 first. Then pSP72-Cpn10-1-ΔC7 was used for site-directed mutagenesis with primers Cpn10-1-C37S-F and Cpn10-1-C37S-R. The sequence was confirmed by sequencing and the plasmid was named pSP72-Cpn10-1-ΔC7C37S. The in vitro expression of prAPS1 and prAPR3 was under the control of the T7 promoter. The in vitro expression of prFibrillin, prAPS3, prsAPX, prTic40-E2A, and prCpn10-1-ΔC7C37S was under the control of the SP6 promoter.

[$^{35}$S]Met-labeled prPDH E1α was generated by in vitro transcription for synthesizing RNA followed by in vitro translation using the Rabbit Reticulocyte Lysate system (PROMEGA). All other precursors were synthesized using the TNT Coupled Wheat Germ Extract system or TNT Coupled Reticulocyte Lysate system (PROMEGA).

TABLE 1

Primers used for cloning in the invention

| Primer | Nucleotide sequence | Purpose |
|---|---|---|
| fibrillin-F1-HindIII | 5'-cgaagcttatggcgacggtacaattgtc-3' SEQ ID NO: 21 | To clone the coding region of prFibrillin into pSP72 |

TABLE 1-continued

Primers used for cloning in the invention

| Primer | Nucleotide sequence | Purpose |
|---|---|---|
| fibrillin-R1-PstI | 5'-cgctgcagtcaaggattcaagagagg-3'<br>SEQ ID NO: 22 | To clone the coding region of prFibrillin into pSP72 |
| APS3-F1-XhoI | 5'-cactcgagatggcttccatgtccaccgtcttcc-3'<br>SEQ ID NO: 23 | To clone the coding region of prAPS3 into pSP72 |
| APS3-R1-SalI | 5'-cagtcgacttaaaccggaatcttttccggaagtt-3'<br>SEQ ID NO: 24 | To clone the coding region of PrAPS3 into pSP72 |
| sAPX-F2-XhoI | 5'-agctcgagatggcagagcgtgtgtctc-3'<br>SEQ ID NO: 25 | To clone the coding region of prsAPX into pSP72 |
| sAPX-R2-SalI | 5'-gcgtcgacttagataacgataccctccg-3'<br>SEQ ID NO: 26 | To clone the coding region of prsAPX into pSP72 |
| fibrillin-2M-F | 5'-tctcttgaatcctatgatgtgactgcaggtcg-3'<br>SEQ ID NO: 27 | To add two extra methionine residues in the C terminus of fibrillin |
| fibrillin-2M-R | 5'-cgacctgcagtcacatcataggattcaagaga-3'<br>SEQ ID NO: 28 | To add two extra methionine residues in the C terminus of fibrillin |
| pSP72-Tic40-E2A-F | 5'-cgataagcttgatatggcgaatcttaacttagccc-3'<br>SEQ ID NO: 29 | To mutate the glutamic acid residue at position 2 of prTic40 into alanine residue |
| pSP72-Tic40-E2A-R | 5'-gggctaagttaagattcgccatatcaagcttatcg-3'<br>SEQ ID NO: 30 | To mutate the glutamic acid residue at position 2 of prTic40 into alanine residue |
| Cpn10-1-ΔC7-F | 5'-gcttccactttcgtctctctaccaaatcct-3'<br>SEQ ID NO: 31 | To delete the cysteine residue at position 2 of prCpn10-1 |
| Cpn10-1-ΔC7-R | 5'-aggatttggtagagagacgaaagtggaagc-3'<br>SEQ ID NO: 32 | To delete the cysteine residue at position 2 of prCpn10-1 |
| Cpn10-1-C37S-F | 5'-cggaagtcgaagaggttcccttagaatcaaagcga-3'<br>SEQ ID NO: 33 | To mutate the cysteine residue at position of 37 of prCpn10-1 into serine |
| Cpn10-1-C37S-R | 5'-tcgctttgattctaagggaacctcttcgacttccg-3'<br>SEQ ID NO: 34 | To mutate the cysteine residue at position of 37 of prCpn10-1 into serine |

EXAMPLE 4

Protein Import into Isolated Plastids and Post-import Analyses

After setting up the leucoplast isolation conditions, the present invention next compared the import behavior of various precursor proteins into leucoplasts and chloroplasts. An equal amount of proteins (Yan et al., 2006) or an equal number of plastids (Wan et al., 1996) was usually used as the basis when comparing among import efficiencies of different plastids. To determine the number of plastids, the isolated leucoplasts and chloroplasts were counted using the Multi-sizer 3 Coulter Counter (BECKMAN COULTER). The present invention used chloroplasts isolated from 7-day-old seedlings for robust import and for decreasing the age difference between the leucoplast and chloroplast samples. The average size of the isolated leucoplasts and chloroplasts was estimated to be 1.81±0.21 μm and 3.24±0.23 μm, respectively. The same plastid preparations were then used for protein concentration determination and the average protein content was calculated to be 1.85±0.63 and 8.13±1.42 μg/plastid for leucoplasts and chloroplasts, respectively. The present invention then used protein content as an estimate of plastid numbers in the experiments thereafter. For example, 500 μg of plastid proteins would represent approximately $2.71 \times 10^8$ leucoplasts and $6.15 \times 10^7$ chloroplasts. For import comparison between chloroplasts and leucoplasts on an equal protein basis, 18 μL [$^{35}$S]Met-labeled precursors were incubated with isolated plastids equivalent to 500 μg plastid proteins in the presence of 3 mM ATP in import buffer in a final volume of 200 μL. For import comparison on an equal plastid number basis, 113.67 μg leucoplast proteins ($2.71 \times 10^8$ leucoplasts) and 500 μg chloroplast proteins ($2.71 \times 10^8$ chloroplasts) were used instead. Import reactions were carried out at room temperature for 25 mM and stopped by transferring to a new tube containing 1 mL ice-cold import buffer. The plastids were pelleted by centrifugation at 3,000 g at 4° C. for 3 mM and re-suspended in 200 μL import buffer. The leucoplast suspensions were underlaid with 1 mL 10% Percoll™ (v/v) in import buffer and the chloroplast suspensions were laid on top of a 40% Percoll™ (v/v) cushion to re-isolate the intact plastids with a swinging-bucket rotor by 2,900 g for 6 mM at 4° C. The plastids were washed once with import buffer and re-suspended in a small volume of import buffer. Protein concentrations of the plastid samples were measured with the BCA protein assay kit (THERMO). Samples were analyzed by SDS-PAGE. Quantification of gel bands was performed using the Fuji FLA5000 PhosphorImager (FUJIFILM, Tokyo).

Figure 1B:
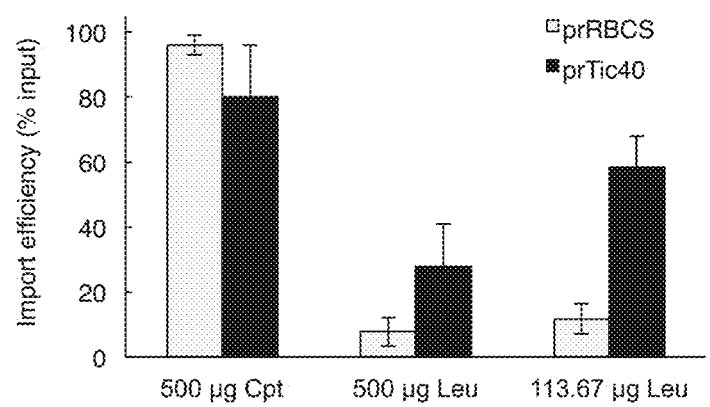

EXAMPLE 5 prRBCS Imported Poorly into Leucoplasts and prTic40 Imported Efficiently into Both Chloroplasts and Leucoplasts To provide quantitative comparison of the import efficiency of prRBCS into chloroplasts and leucoplasts, import was compared based on equal proteins or on equal plastid numbers. The results showed that the import efficiency of prRBCS into leucoplasts was much lower than its import efficiency into chloroplasts no matter whether the comparison was done on an equal amount of proteins or on an equal number of plastids basis (FIGS. 1A and 1B). Furthermore, in initial screenings from our original collection of precursor proteins, prTic40 showed the best import activity into isolated leucoplasts and it was therefore used to compare with prRBCS. prTic40 imported into chloroplasts with similar efficiency to prRBCS, and imported into leucoplast much more efficiently than prRBCS.

EXAMPLE 6

Identification of Transit Peptides with High Leucoplast Import Efficiencies

Figure 2A:
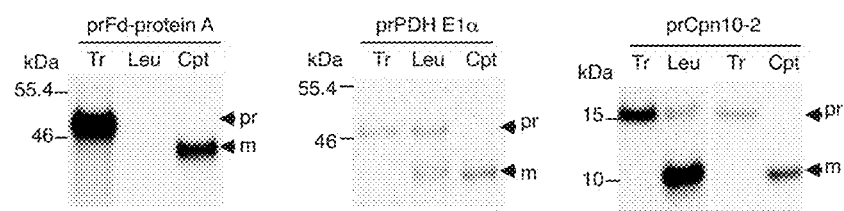
FIGS. 2A and 2B show that different precursor proteins had different plastid preference. The precursor prFd-protein A serves as an example of highly preferring chloroplasts. The precursor prPDH E1α serves as an example of mildly preferring chloroplasts. The precursor prCpn10-2 serves as an example of showing no preference and being able to import well into both chloroplasts and leucoplasts.
Figure 2B:
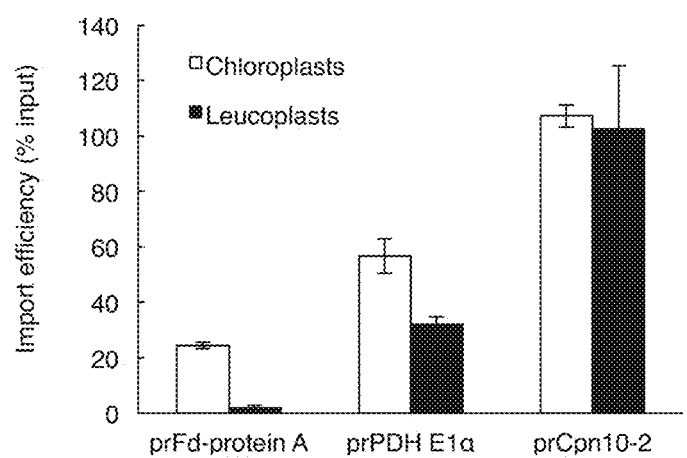

The present invention further tested another three precursors, ferredoxin precursor (prFd), pyruvate dehydrogenase E1α subunit precursor (prPDH E1α), and chaperonin 10-2 (prCpn10-2) precursor, to confirm that different precursors have different plastid preferences. For prFd, the present invention used the construct prFd-protein A, which contains ferredoxin transit peptide fused to Staphylococcal protein A, as described (Smith et al., 2004). As shown in FIGS. 2A and 2B, prFd-protein A imported efficiently into chloroplasts but minimally imported into leucoplasts, similar to the results of prRBCS. In comparison, although prPDH E1α also imported more efficiently into chloroplasts, but its import into leucoplasts was about half that of chloroplasts. In comparison, prCpn10-2 imported equally well into both chloroplasts and leucoplasts.

Figure 3A:
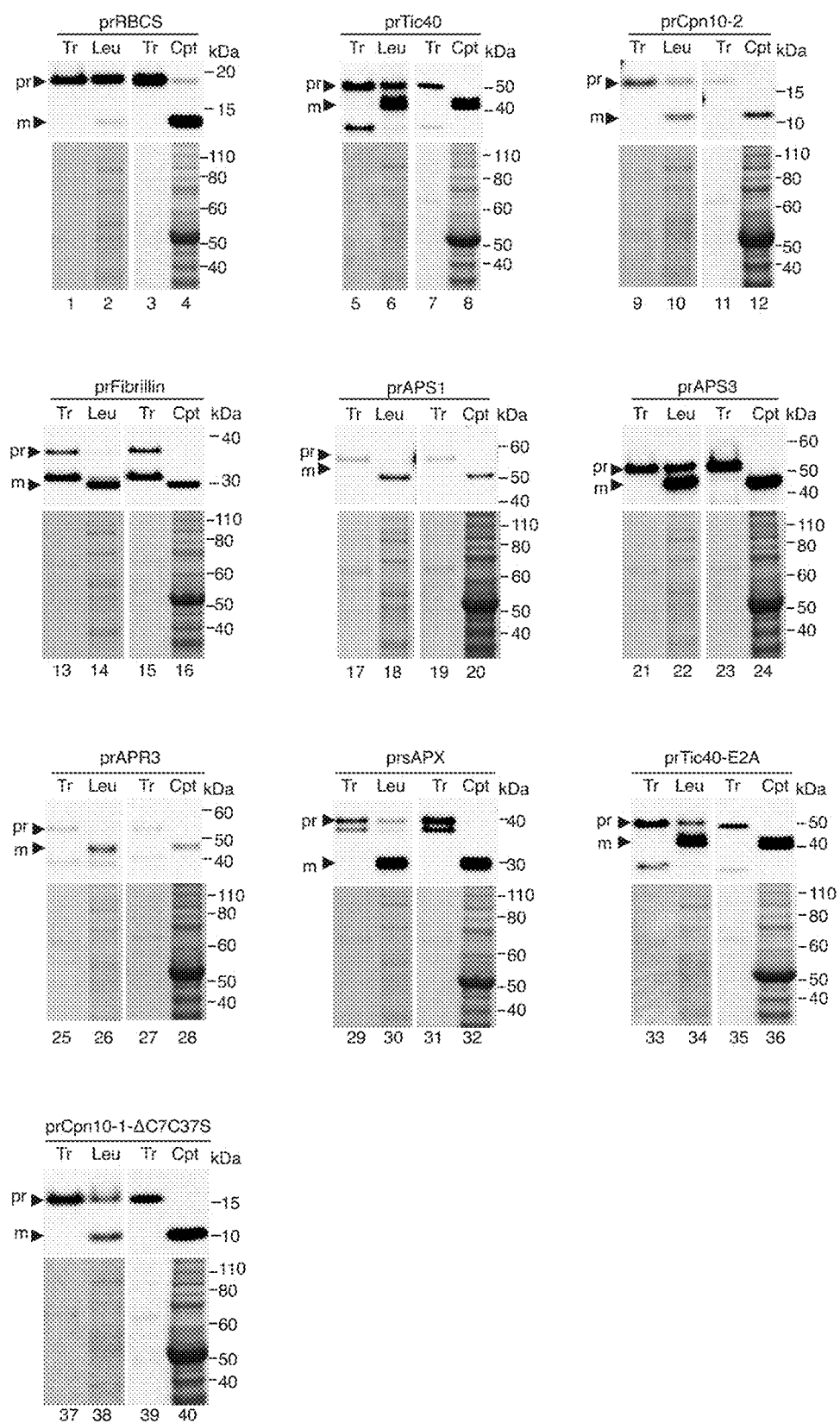
FIGS. 3A to 3C show that nine precursor proteins had high import efficiencies into both leucoplasts and chloroplasts, and these nine precursor proteins all had much higher leucoplast import efficiency than prRBCS.
Figure 3B:
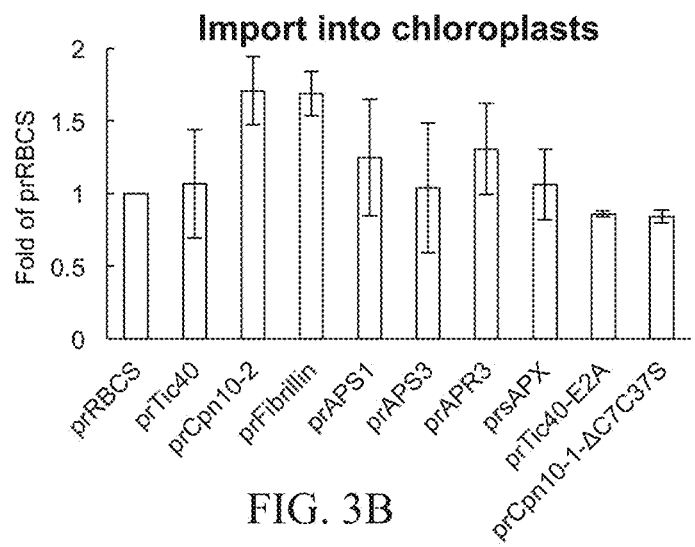
Figure 3C:
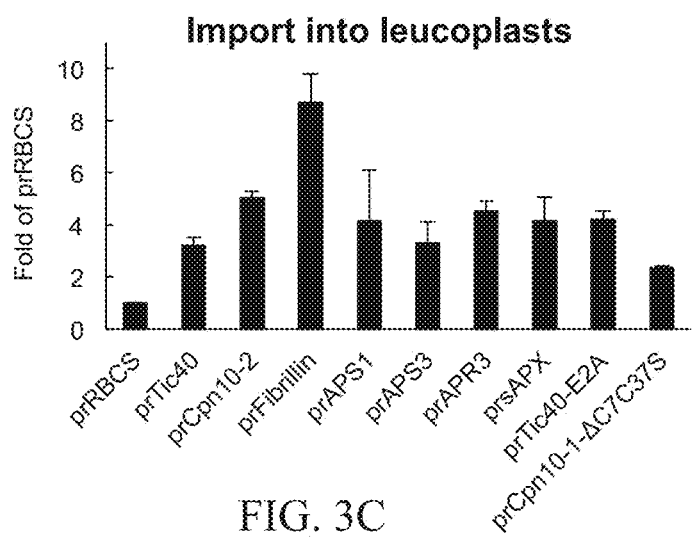

Precursors like prTic40 and prCpn10-2 are of particular interests because they can import very efficiently into both chloroplasts and leucoplasts. The present invention further cloned and tested the import of more than 60 plastid precursor proteins from *Arabidopsis* in the leucoplast import system the present invention set up. The present invention found another five precursors that also exhibited very high import efficiency into both chloroplasts and leucoplasts (FIGS. 3A to 3C and Table 2). They include precursors to Fibrillin 1B (prFibrillin), ATP sulfurylase 1 (prAPS1) and 3 (prAPS3), 5'-adenylylsulfate reductase 3 (prAPR3) and stromal ascorbate peroxidase (prsAPX). Another two precursor variants, prTic40-E2A and prCpn10-1-ΔC7C37S, also showed high import efficiency into both chloroplasts and leucoplasts (FIGS. 3B and 3C and Table 2). For these nine precursors, their chloroplast import efficiency was comparable to that of prRBCS (FIG. 3B), but their leucoplast import efficiency was 2~8 times higher than that of prRBCS (FIG. 3C).

TABLE 2

Transit peptides with high import efficiencies in plastids. Amino acids of the transit peptide are shown in lowercase letters and the first three amino acids in the mature region are shown in capital letters. The prRBCS transit peptide used as a control is also shown here.

| Precursors (Accession number) | Full name | Nucleotide sequences | Transit peptide sequence |
|---|---|---|---|
| prTic40 (AY157668) | Translocon at the inner envelope membrane of chloroplasts 40 kD | atggagaatc ttaacttagc ccttgtttct tcccctaaac ccctgctttt aggacattcc tcctcaaaaa acgttttctc aggaaggaag tctttcactt tgggacgtt tcgcgtttct gctaactctt catcctctca tgtcaccagg gctgcttcta aatctcacca aaatctaaaa tctgtgcagg ggaaggtgaa tgcgcatgat tttgctagc SEQ ID NO: 1 | menlnlalvs spkplllghs ssknvfsgrk sftfgtfrvs anssshvtr aaskshqnlk svqgkvnahd FAS SEQ ID NO: 10 |
| prCpn10-2 (AT3G60210) | chaperonin 10-2 | atggcttcga gtttcattac agtacctaaa cccttcttgt ccttccccat caaaaccaat gctcctactc tacctcagca gacccttctc ggaattcgaa gaaattcctt tagaattaac gccgtttcc SEQ ID NO: 2 | massfitvpk pflsfpiktn aptlpqqtll girrnsfrin AVS SEQ ID NO: 11 |
| prFibrillin 1B (AT4G22240) | Fibrillin 1B | atggcgacgg tacaattgtc cacccaattt agctgccaaa ccagagtttc aatctcaccg aactctaaat ctatctccaa gcctccgttt ctggtaccgg tgacctcaat tattcaccgc ccgatgatct ccaccggagg aatcgctgtt tcccccgta gagttttcaa agtccgagcc acagatacgg gagagatagg atcagctcta ttggcggcgg aggaagca SEQ ID NO: 3 | matvqlstqf scqtrvsisp nsksiskppf lvpvtsiihr pmistggiav sprrvfkvra tdtgeigsal laaEEA SEQ ID NO: 12 |
| prAPS1 (AT3G22890) | ATP sulfurylase 1 | atggcttcaa tggctgccgt cttaagcaaa actccattcc tctctcaacc actaaccaaa tcatctccaa actccgatct cccccttcgcc | masmaavlsk tpflsqpltk sspnsdlpfa avsfpskslr rrvgsiragl iapdggklve |

TABLE 2-continued

Transit peptides with high import efficiencies in plastids. Amino acids of the transit peptide are shown in lowercase letters and the first three amino acids in the mature region are shown in capital letters. The prRBCS transit peptide used as a control is also shown here.

| Precursors (Accession number) | Full name | Nucleotide sequences | Transit peptide sequence |
|---|---|---|---|
| | | gcggtttcct tcccttccaa atccctacgc cgccgcgtag gatcaatccg agccggatta atcgctcccg acggtggtaa gcttgtagag ctcatcgtgg aagagccaaa gcggcgagag aagaaacacg ag SEQ ID NO: 4 | liveepkrre kKHE SEQ ID NO: 13 |
| prAPS3 (AT4G14680) | ATP sulfurylase 3 | atggcttcca tgtccaccgt cttccccaaa ccaacctctt tcatctctca acctctaaca aaatctcaca aatccgattc cgtaaccaca tccatttcat tcccttgaa ttcgaaaact cgtagcttaa gaaccatctc tgtacgagct ggcttaatcg agccagatgg tgggaaactt gtggatcttg ttgtaccgga accgagacgg cgagagaaga aa SEQ ID NO: 5 | masmstvfpk ptsfisqplt kshksdsvtt sisfpsnskt rslrtisvra gliepdggkl vdlvvpeprr rEKK SEQ ID NO: 14 |
| prAPR3 (AT4G21990) | 5'-adenylyl-sulfate reductase 3 | atggcactag caatcaacgt ttcttcatct tcttcttctg cgatctcaag ctctagcttc cctccttcag atctcaaagt aacaaaaatc ggatcattga ggttattgaa tcgtaccaat gtctctgcgg cttctctgag tttgtccggg aagagatcct ccgtgaaagc tcttaatgtg caatcaatta caaaggaatc cattgttgct tctgaggtta cagagaagct agatgtggtg gaagttgaa SEQ ID NO: 6 | malainvsss sssaissssf pssdlkvtki gslrllnrtn vsaaslslsg krssvkalnv qsitkesiva sevtekldvv EVE SEQ ID NO: 15 |
| prsAPX (AT4G08390) | stromal ascorbate peroxidase | atggcagagc gtgtgtctct cacactcaac ggaaccctcc tttctcctcc tcccacaaca acaacaacaa caatgtcttc ttctctccga tctaccaccg ccgcttctct tctcctccgc tcctcctcct cctcctccag atccactctc SEQ ID NO: 7 | maervsltln gtllsppptt ttttmssslr sttaaslllr ssssssrSTL SEQ ID NO: 16 |
| prTic40-E2A (AY157668 variant) | Translocon at the inner envelope membrane of chloroplasts 40 kD variant | atggcgaatc ttaacttagc ccttgtttct tccctaaac ccctgctttt aggacattcc tcctcaaaaa acgttttctc aggaaggaag tctttcactt ttgggacgtt tcgcgtttct gctaactctt catcctctca tgtcaccagg gctgcttcta aatctcacca aaatctaaaa tctgtgcagg ggaaggtgaa tgcgcatgat tttgctagc SEQ ID NO: 8 | manlnlalvs spkplllghs ssknvfsgrk sftfgtfrvs ansssshvtr aaskshqnlk svqgkvnahd FAS SEQ ID NO: 17 |
| prCpn10-1-ΔC7C37S (AT2G44650 variant) | chaperonin 10-1 variant | atggcttcca ctttcgtctc tctaccaaat ccttttcttg cttttccggt caaagcaact actccttcga cggctaacca tacgcttctc ggaagtcgaa gaggttccct tagaatcaaa gcgatttcc SEQ ID NO: 9 | mastfvslpn pffafpvkat tpstanhtll gsrrgslrik AIS SEQ ID NO: 18 |
| prRBCS (NM 001248385) | Ribulose-1,5-bisphosphate carboxylase small subunit | atggcttcct caatgatctc ctccccagct gttaccaccg tcaaccgtgc cggtgccggc atggttgctc cattcaccgg cctcaaatcc atggctggct tccccacgag gaagaccaac aatgacatta cctccattgc tagcaacggt ggaagagtac aatgcatgca ggtg SEQ ID NO: 10 | massmisspa vttvnragag mvapftglks magfptrktn nditsiasng grvqcMQV SEQ ID NO: 20 |

EXAMPLE 7

Plasmid Construction for in Vivo Expression of Fusion Proteins in Tobacco BY-2 Suspension Culture Cells and Rice Calli Plasmids for transient in vivo expression were prepared as follows. The coding region corresponding to the transit peptide and the first three amino acids in the mature region of prRBCS, prTic40, prCpn10-2, prFibrillin, prAPS1, prAPS3, prAPR3, prsAPX, prTic40-E2A, prCpn10-1-ΔC7C37S (Table 2) were amplified by PCR using a forward primer that added a XbaI site and a reverse primer that added a BamHI site to the amplified fragment. The PCR fragment for each transit peptide was digested and cloned into the XbaI/BamHI site of the plasmid p326GFP (Lee et al., 2002), resulting in translational fusion of the transit peptide to the N terminus of GFP. The sequence was confirmed by sequencing and the plasmid was named prRBCS$_{tp}$-GFP, prTic40$_{tp}$-GFP, prCpn10-2$_{tp}$-GFP, prFibrillin$_{tp}$-GFP, prAPS1$_{tp}$-GFP, prAPS3$_{tp}$-GFP, prAPR3$_{tp}$-GFP, prsAPX$_{tp}$-GFP, prTic40-E2A$_{tp}$-GFP and prCpn10-1-ΔC7C37S$_{tp}$-GFP, respectively. The transit peptide-GFP fusion constructs were placed under the control of the cauliflower mosaic virus 35S (CaMV35S) promoter and the nopaline synthase (nos) terminator. These transit peptide-GFP fusion constructs were co-transformed with the plasmid pBI221, which contains CaMV35S driven β-glucuronidase (GUS) gene and serves as an internal control for transformation and protein expression efficiency. Protoplasts isolated from tobacco BY-2 suspension cells were transformed by polyethylene glycol mediated transformation. The amounts of GFP and GUS protein produced were determined by immunoblotting. The efficiency of each transit peptide was calculated by the amount of GFP produced normalized to the amount of GUS produced for each transformation. Rice embryo-induced calli were transformed by particle bombardment and Agrobacteria-mediated transformation. Multiple transformation experiments were performed for each construct and the average efficiency of each transit peptide was calculated and compared to the average efficiency of prRBCS transit peptide. The subcellular localization of the expressed proteins was confirmed by confocal microscopy.

EXAMPLE 8

Figure 4A:
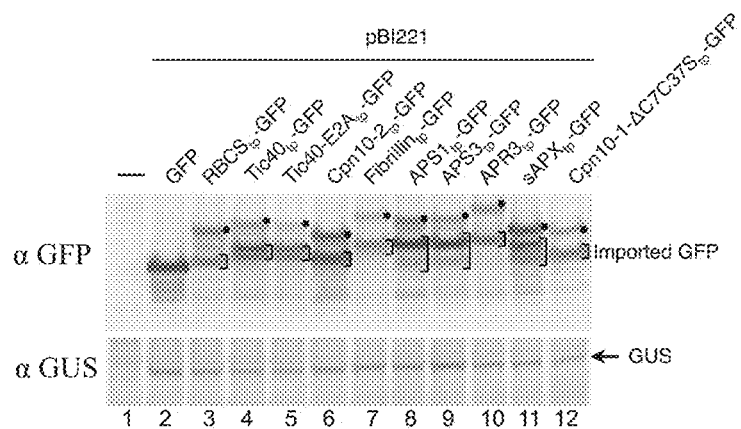
FIGS. 4A and 4B show that the nine high-efficiency transit peptides of the present invention indeed delivered a higher amount of passenger proteins into leucoplasts than the prRBCS transit peptide.
Figure 4B:
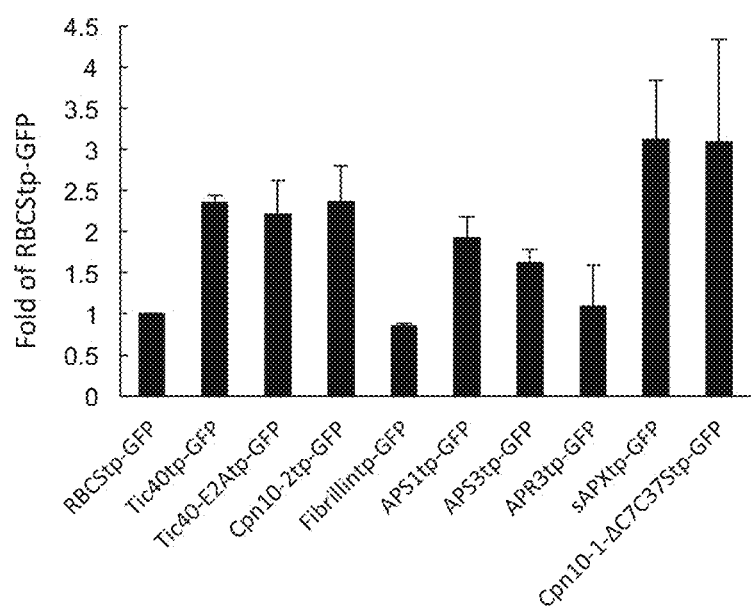

Demonstration of Transit Peptide Efficiency by in Vivo Expression of Fusion Proteins The present invention further fused the transit peptides from the nine high-import-efficiency precursors to GFP as described above and tested the in vivo leucoplast import efficiency of these nine fusion proteins. The present invention used transient expression in tobacco BY-2 suspension culture cells and rice calli, which are widely used and represent established model systems for non-green leucoplast-containing tissues of dicotyledon and monocotyledon plants, respectively. Both systems can be easily transformed and served as a quick and reliable tool for evaluating the in vivo leucoplast import efficiency of the fusion proteins. The results (FIGS. 4 A and B) showed that, when GFP was fused to eight of nine transit peptides of the present invention, the amount of GFP imported into leucoplasts was much higher than when GFP was fused to the transit peptide of prRBCS. One of the transit peptides of the present invention had a similar efficiency to the prRBCS transit peptide.

EXAMPLE 9

Plasmid Construction and Protein Expression in Transgenic *Arabidopsis* Plants

The DNA fragment encoding GFP from the plasmid p326GFP (Lee et al., 2002) was amplified by PCR using a forward primer that added a BamHI site and a reverse primer that added an XbaI site to the amplified fragments. The fragment was digested and cloned into the BamHI/XbaI site of pSP72. The sequences were confirmed by sequencing and the plasmid was named pSP72-GFP. The DNA fragments encoding the transit peptide and the first three amino acids of the mature region of prRBCS, prTic40, prCpn10-2, prFibrillin, prAPS3, prAPR3, prsAPX, prTic40-E2A, prCpn10-1-ΔC7C37S (Table 2) were amplified by PCR using a forward primer that added a SacI site and a reverse primer that added a BamHI site to the amplified fragment. The fragments were digested and cloned into the SacI/BamHI site of pSP72-GFP to generate the transit peptide-GFP fusion constructs. The DNA fragment encoding the transit peptide and the first three amino acids of the mature region of prAPS1 was amplified by PCR using a forward primer that added a KpnI site and a reverse primer that added a BamHI site to the amplified fragment. The fragments were digested and cloned into the KpnI/BamHI site of pSP72-GFP. All sequences were confirmed by sequencing. The DNA fragments encoding the transit peptide-GFP were excised by SacI/PstI (for prRBCS$_{tp}$-GFP, prTic40$_{tp}$-GFP, prCpn10-2$_{tp}$-GFP, prFibrillin$_{tp}$-GFP, prAPS3$_{tp}$-GFP, prAPR3$_{tp}$-GFP, prsAPX$_{tp}$-GFP, prTic40-E2A$_{tp}$-GFP and prCpn10-1-ΔC7C37S$_{tp}$-GFP) and KpnI/PstI (for prAPS1$_{tp}$-GFP) and cloned into the SacI/PstI site and KpnI/PstI site of the binary vector pCHF1 (Hajdukiewicz et al., 1994), respectively. The transit peptide-GFP fusion constructs were placed under the control of the CaMV35S promoter and the RBCS terminator. The resulting plasmids were transformed into *Agrobacterium tumefaciens* GV3101. *Arabidopsis* (Columbia ecotype) plants will be transformed by the floral spray method (Chung et al., 2000). Transgenic plants harboring the introduced transit peptide-GFP fusion transgene will be identified on MS medium containing 100 μg/mL G418. Multiple independent transgenic plants will be obtained for each transit peptide-GFP construct. The RNA and protein amount of the expressed GFP will be detected by quantitative RT-PCR and immunoblotting. The localization of GFP in root leucoplasts will be verified by confocal microscopy. The size of GFP should also be the processed mature-size GFP on immunoblots, corroborating with delivery to plastids and removal of the transit peptide. After normalization to the GFP RNA level, the efficiency of each transit peptide in delivering GFP to root leucoplasts in each transgenic plant will be calculated. The average efficiency of each transit peptide will be compared to the average efficiency of prRBCS transit peptide. The efficiency of each transit peptide in delivering GFP to leaf chloroplasts will also be compared to that of prRBCS transit peptide. It is expected that the efficiency of each of the high-efficiency transit peptides as described herein, in delivering GFP to chloroplasts, will be equal or higher than that of prRBCS transit peptide. It is further expected that the efficiency of each of the high-efficiency transit peptides as described herein, in delivering GFP to leucoplasts, will be higher than that of prRBCS transit peptide.

The present invention provides a group of nine transit peptides that have very high import efficiency into both chloroplasts and leucoplasts. They are transit peptides of the precursors of translocon at the inner envelope membrane of chloroplasts 40 kD (prTic40), chaperonin 10-2 (prCpn10-2), Fibrillin 1B (prFibrillin), ATP sulfurylase 1 (prAPS1), ATP sulfurylase 3 (prAPS3), 5'-adenylylsulfate reductase 3 (prAPR3), stromal ascorbate peroxidase (prsAPX), prTic40-E2A (a prTic40 variant) and prCpn10-1-ΔC7C37S (a chaperonin 10-1 variant). These nine transit peptides of the present invention all have similarly high chloroplast-import efficiency, and much higher leucoplast-import efficiency, than the prRBCS transit peptide. The more than 60 precursors the present invention tested and the nine precursors of the present invention have never been tested for leucoplast import before. The transit peptide of prRBCS is the most widely used transit peptide for delivering engineered proteins into plastids. Examples include the famous Golden Rice, Roundup Ready® corn and Dicamba resistant soybean. In the case of Golden rice, for example, they have used the prRBCS transit peptide to deliver the bacterial carotene desaturase into rice grain leucoplasts. The present invention has shown quantitatively here that, for delivering proteins into leucoplasts, the nine transit peptides of the present invention are much more efficient than the prRBCS transit peptide. If the one of ordinary skill in the art had used one of the transit peptides from the present invention, the production of provitamin A in the rice grains may be even higher. The next step is to test which of the nine transit peptides offer the highest protein import efficiency into plastids in stably transformed plants.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A recombinant DNA molecule encoding a fusion protein, wherein said recombinant DNA molecule comprises a first DNA sequence encoding a transit peptide operably linked to a second DNA sequence encoding a passenger protein, wherein the transit peptide consists of the first 40 amino acids of SEQ ID NO: 13 and wherein the transit peptide is heterologous to the passenger protein.

2. A DNA construct comprising the recombinant DNA molecule according to claim 1, wherein said recombinant DNA molecule is operably linked to a promoter.

3. The DNA construct according to claim 2, wherein the promoter is functional in a plant cell.

4. A plant material comprising the DNA construct according to claim 3.

5. The plant material according to claim 4, wherein the plant material is selected from the group consisting of a plant cell, a plant tissue, a plant tissue culture, a callus culture and a transgenic plant.

6. The plant material according to claim 4, wherein the plant material is obtained from a monocotyledon or a dicotyledon plant.

7. A method of delivering a passenger protein into leucoplasts, comprising:
  (a) providing a recombinant DNA molecule encoding a fusion protein;
  (b) linking the recombinant DNA molecule operably with a promoter to form a DNA construct, wherein the promoter is functional in a plant cell; and
  (c) introducing the DNA construct into a plant material to express the fusion protein; wherein the recombinant DNA molecule comprises a first DNA sequence encoding a transit peptide operably linked to a second DNA sequence encoding a passenger protein, wherein the transit peptide consists of the first 40 amino acids of SEQ ID NO: 13 and wherein the transit peptide is heterologous to the passenger protein.

8. The method according to claim 7, wherein the plant material is selected from the group consisting of a plant cell, a plant tissue, a plant tissue culture, a callus culture and a transgenic plant.

9. The method according to claim 7, wherein the plant material is obtained from a monocotyledon or a dicotyledon plant.

* * * * *